(12) United States Patent
Markham et al.

(10) Patent No.: US 9,478,959 B2
(45) Date of Patent: Oct. 25, 2016

(54) LASER WELDING A FEEDTHROUGH

(71) Applicant: Heraeus Precious Metals GmbH & Co. KG, Hanau (DE)

(72) Inventors: Jacob Markham, Vadnais Heights, MN (US); Ulrich Hausch, Frankfurt (DE); Goran Pavlovic, Schaafheim (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 749 days.

(21) Appl. No.: 13/804,888

(22) Filed: Mar. 14, 2013

(65) Prior Publication Data

US 2014/0262493 A1  Sep. 18, 2014

(51) Int. Cl.
*B23K 26/20* (2014.01)
*B23K 26/26* (2014.01)
*H02G 3/22* (2006.01)
*A61N 1/375* (2006.01)

(52) U.S. Cl.
CPC .............. *H02G 3/22* (2013.01); *A61N 1/3754* (2013.01); *B23K 26/20* (2013.01); *B23K 26/206* (2013.01); *B23K 26/26* (2013.01); *Y10T 29/49227* (2015.01)

(58) Field of Classification Search
CPC .... B23K 26/20; B23K 26/206; B23K 26/26; B23K 26/324
See application file for complete search history.

(56) References Cited

U.S. PATENT DOCUMENTS

| | | | |
|---|---|---|---|
| 3,979,187 A | 9/1976 | Scherer | |
| 4,152,540 A | 5/1979 | Duncan et al. | |
| 4,217,137 A | 8/1980 | Kraska et al. | |
| 4,315,054 A | 2/1982 | Sack et al. | |
| 4,352,951 A | 10/1982 | Kyle | |
| 4,354,964 A | 10/1982 | Hing et al. | |
| 4,362,792 A | 12/1982 | Bowsky et al. | |
| 4,456,786 A | 6/1984 | Kyle | |
| 4,488,673 A | 12/1984 | Hopper, Jr. | |
| 4,602,956 A | 7/1986 | Partlow et al. | |

(Continued)

FOREIGN PATENT DOCUMENTS

| | | |
|---|---|---|
| DE | 69729719 | 7/2005 |
| DE | 102006054249 | 5/2008 |

(Continued)

OTHER PUBLICATIONS

Hussain, et al., "Electrical conductivity of an insulator matrix (alumina) and conductor particle (molybdenum) composites", Journal of the European Ceramic Society, vol. 23, Issue 2, Feb. 2003, pp. 315-321.

(Continued)

*Primary Examiner* — Geoffrey S Evans
(74) *Attorney, Agent, or Firm* — Dicke, Billig & Czaja, PLLC

(57) ABSTRACT

One aspect is a method of coupling an insulator to a surrounding ferrule in an implantable medical device. An insulator is provided having a plurality of conducting elements extending therethrough. The insulator is placed with conducting elements within a ferrule having a frame-like shape surrounding the insulator along an interface. The insulator is heated with a first laser until raising the temperature of insulator to a first temperature level. The ferrule is welded to the insulator along the interface with a second laser once the insulator has reached the first temperature.

14 Claims, 6 Drawing Sheets

(56) References Cited

U.S. PATENT DOCUMENTS

| | | |
|---|---|---|
| 4,678,868 A | 7/1987 | Kraska et al. |
| 4,737,601 A | 4/1988 | Gartzke |
| 4,774,953 A | 10/1988 | Foote |
| 4,782,209 A * | 11/1988 | Caers ............... C03C 27/046 |
| | | 219/121.64 |
| 4,816,621 A | 3/1989 | Huebner et al. |
| 4,991,582 A | 2/1991 | Byers et al. |
| 4,992,910 A | 2/1991 | Evans |
| 5,043,535 A | 8/1991 | Lin |
| 5,046,262 A | 9/1991 | Kerbaugh |
| 5,245,999 A | 9/1993 | Dahlberg et al. |
| 5,272,283 A | 12/1993 | Kuzma |
| 5,306,891 A * | 4/1994 | Fleming ............... C04B 37/026 |
| | | 219/121.64 |
| 5,333,095 A | 7/1994 | Stevenson et al. |
| 5,407,119 A | 4/1995 | Churchill et al. |
| 5,408,066 A | 4/1995 | Trapani et al. |
| 5,513,793 A | 5/1996 | Malmgren |
| 5,515,604 A | 5/1996 | Horine et al. |
| 5,654,106 A | 8/1997 | Purnell et al. |
| 5,683,435 A | 11/1997 | Truex et al. |
| 5,738,270 A | 4/1998 | Malmgren |
| 5,750,926 A | 5/1998 | Schulman et al. |
| 5,769,874 A | 6/1998 | Dahlberg |
| 5,782,891 A | 7/1998 | Hassler et al. |
| 5,796,019 A | 8/1998 | Lupton et al. |
| 5,821,011 A | 10/1998 | Taylor et al. |
| 5,851,222 A | 12/1998 | Taylor et al. |
| 5,855,711 A | 1/1999 | Araki et al. |
| 5,861,714 A | 1/1999 | Wei et al. |
| 5,866,851 A | 2/1999 | Taylor et al. |
| 5,870,272 A | 2/1999 | Seifried et al. |
| 5,905,627 A | 5/1999 | Brendel et al. |
| 6,093,476 A | 7/2000 | Horiuchi et al. |
| 6,232,004 B1 | 5/2001 | Lasater |
| 6,284,080 B1 | 9/2001 | Haq et al. |
| 6,414,835 B1 | 7/2002 | Wolf et al. |
| 6,579,492 B2 | 6/2003 | Wehler |
| 6,586,675 B1 | 7/2003 | Bealka et al. |
| 6,643,903 B2 | 11/2003 | Stevenson et al. |
| 6,660,116 B2 | 12/2003 | Wolf et al. |
| 6,999,818 B2 | 2/2006 | Stevenson et al. |
| 7,035,076 B1 | 4/2006 | Stevenson |
| 7,035,077 B2 * | 4/2006 | Brendel ............... H01G 4/35 |
| | | 361/302 |
| 7,038,900 B2 | 5/2006 | Stevenson et al. |
| 7,068,491 B1 | 6/2006 | Burdon et al. |
| 7,107,099 B1 | 9/2006 | O'Phelan et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,222,419 B2 | 5/2007 | Horng et al. |
| 7,260,434 B1 | 8/2007 | Lim et al. |
| 7,274,963 B2 | 9/2007 | Spadgenske |
| 7,437,817 B2 | 10/2008 | Zhang et al. |
| 7,480,988 B2 | 1/2009 | Ok et al. |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,569,452 B2 | 8/2009 | Fu et al. |
| 7,630,768 B1 | 12/2009 | Coffed et al. |
| 7,668,597 B2 | 2/2010 | Engmark et al. |
| 7,706,124 B2 | 4/2010 | Zhao et al. |
| 7,720,538 B2 | 5/2010 | Janzig et al. |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,818,876 B2 | 10/2010 | Suaning |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 | 8/2011 | Wessendorf et al. |
| 8,065,009 B2 | 11/2011 | Biggs |
| 8,131,369 B2 | 3/2012 | Taylor et al. |
| 8,131,376 B1 | 3/2012 | Faraji et al. |
| 8,155,743 B2 | 4/2012 | Rundle et al. |
| 8,163,397 B2 | 4/2012 | Ok et al. |
| 8,179,658 B2 | 5/2012 | Brendel et al. |
| 8,189,333 B2 | 5/2012 | Foster |
| 8,288,654 B2 | 10/2012 | Taylor et al. |
| 8,346,362 B2 | 1/2013 | Kinney et al. |
| 8,355,785 B1 | 1/2013 | Hammond et al. |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,552,311 B2 | 10/2013 | Koester et al. |
| 8,656,736 B2 | 2/2014 | Terao |
| 8,659,870 B2 | 2/2014 | Brendel et al. |
| 8,742,268 B2 | 6/2014 | Reisinger et al. |
| 8,755,887 B2 | 6/2014 | Troetzschel et al. |
| 8,825,162 B2 | 9/2014 | Reisinger |
| 8,886,320 B2 | 11/2014 | Troetzschel et al. |
| 8,894,914 B2 | 11/2014 | Pavlovic |
| 8,929,987 B2 | 1/2015 | Troetzschel et al. |
| 2001/0013756 A1 | 8/2001 | Mori et al. |
| 2001/0018012 A1 | 8/2001 | Harmand et al. |
| 2001/0041227 A1 | 11/2001 | Hislop |
| 2002/0166739 A1 | 11/2002 | Naerheim |
| 2003/0109903 A1 | 6/2003 | Berrang et al. |
| 2004/0023101 A1 | 2/2004 | Jacobson et al. |
| 2004/0116976 A1 | 6/2004 | Spadgenske |
| 2004/0128016 A1 | 7/2004 | Stewart |
| 2006/0025866 A1 | 2/2006 | Serafin, Jr. et al. |
| 2006/0247714 A1 | 11/2006 | Taylor et al. |
| 2006/0259093 A1 | 11/2006 | Stevenson et al. |
| 2007/0041164 A1 | 2/2007 | Greenberg et al. |
| 2007/0183118 A1 | 8/2007 | Fu et al. |
| 2007/0217121 A1 | 9/2007 | Fu et al. |
| 2007/0276389 A1 | 11/2007 | Franke et al. |
| 2008/0060834 A1 | 3/2008 | Eck et al. |
| 2008/0071313 A1 | 3/2008 | Stevenson et al. |
| 2008/0119906 A1 | 5/2008 | Starke |
| 2008/0203917 A1 | 8/2008 | Maya |
| 2008/0269831 A1 | 10/2008 | Erickson |
| 2009/0192578 A1 | 7/2009 | Biggs |
| 2009/0281586 A1 | 11/2009 | Lim |
| 2010/0023086 A1 | 1/2010 | Lim |
| 2010/0109966 A1 | 5/2010 | Mateychuk et al. |
| 2010/0121438 A1 | 5/2010 | Jarvik |
| 2010/0241206 A1 | 9/2010 | Truex et al. |
| 2010/0258342 A1 | 10/2010 | Parker |
| 2010/0258540 A1 * | 10/2010 | Tamura ............... B23K 26/067 |
| | | 219/121.64 |
| 2011/0032658 A1 | 2/2011 | Iyer |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0094768 A1 | 4/2011 | Davis et al. |
| 2011/0106228 A1 | 5/2011 | Reiterer et al. |
| 2011/0186349 A1 | 8/2011 | Troetzschel et al. |
| 2011/0190885 A1 | 8/2011 | Troetzschel et al. |
| 2011/0232961 A1 | 9/2011 | Teske |
| 2011/0232962 A1 | 9/2011 | Teske |
| 2012/0006576 A1 | 1/2012 | Barry et al. |
| 2012/0127627 A1 | 5/2012 | Brendel et al. |
| 2012/0193117 A1 | 8/2012 | Specht et al. |
| 2012/0193118 A1 | 8/2012 | Kempf et al. |
| 2012/0193119 A1 | 8/2012 | Kempf et al. |
| 2012/0193125 A1 | 8/2012 | Pavlovic et al. |
| 2012/0193141 A1 | 8/2012 | Reisinger et al. |
| 2012/0194981 A1 | 8/2012 | Kempf et al. |
| 2012/0197326 A1 | 8/2012 | Pavlovic |
| 2012/0197327 A1 | 8/2012 | Specht |
| 2012/0197335 A1 | 8/2012 | Reisinger |
| 2012/0197368 A1 | 8/2012 | Reisinger |
| 2012/0200011 A1 | 8/2012 | Pavlovic |
| 2012/0203294 A1 | 8/2012 | Troetzschel |
| 2013/0035733 A1 | 2/2013 | Breyen et al. |

(56) References Cited

U.S. PATENT DOCUMENTS

| | | |
|---|---|---|
| 2013/0060312 A1 | 3/2013 | Iyer et al. |
| 2013/0184797 A1 | 7/2013 | Tang et al. |
| 2013/0299233 A1 | 11/2013 | Troetzschel et al. |
| 2014/0008121 A1 | 1/2014 | Troetzschel et al. |
| 2014/0144014 A1 | 5/2014 | Troetzschel et al. |
| 2014/0262494 A1 | 9/2014 | Reisinger et al. |
| 2014/0368298 A1 | 12/2014 | Reisinger |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| DE | 102011119125 | 5/2013 |
| EP | 0877400 | 11/1998 |
| EP | 0916364 | 5/1999 |
| EP | 1685874 | 8/2006 |
| EP | 1754511 | 2/2007 |
| EP | 2398026 | 12/2011 |
| JP | 1-148760 A * | 6/1989 |
| JP | 2-133378 A * | 5/1990 |
| WO | 03073450 | 9/2003 |
| WO | 2004110555 | 12/2004 |
| WO | 2008103166 | 8/2008 |
| WO | 2010091435 | 8/2010 |
| WO | 2013075797 | 5/2013 |

OTHER PUBLICATIONS

International Search Report and the Written Opinion for International Application No. PCT/US2014/026011 mailed Nov. 5, 2014 (13 pages).

Exner, Horst et al., "Laser Joining of Ceramics in Liquid Phase," pp. 1-8 (Nov. 8, 2011).

Gil et al., "Grain Growth Kinetics of Pure Titanium," Scripta Metallurgica et Materialia, vol. 33, No. 8, pp. 1361-1366 (Oct. 15, 1995).

* cited by examiner

LASER WELDING A FEEDTHROUGH

BACKGROUND

One aspect relates to a feedthrough device for an implantable medical device. Feedthroughs establish an electrical connection between a hermetically sealed interior and an exterior of the medical device. Known implantable therapeutic devices include cardiac pacemakers or defibrillators, which usually include a hermetically sealed metal housing, which is provided with a connection body, also called header, on one side. Said connection body includes a connection socket for connecting electrode leads. In this context, the connection socket includes electrical contacts that serve to electrically connect electrode leads to the control electronics in the interior of the housing of the implantable therapeutic device—also called implantable device. An essential prerequisite for an electrical bushing of this type is hermetic sealing with respect to the surroundings.

Accordingly, it needs to be made sure that the conducting wires that are introduced into an insulation element and via which the electrical signals proceed, are introduced into the insulation element without any gaps. In this context, it has proven to be disadvantageous that the conducting wires in general are made of a metal and need to be introduced into a ceramic insulation element. In order to ensure long-lasting connection between the two elements, the internal surface of the bore hole in the insulation element must be metallized for soldering the conducting wires into them. Said metallization inside the bore hole in the insulation element has proven to be difficult to apply. Homogeneous metallization of the internal surface of the bore hole in the insulation element can be ensured only by means of expensive procedures. Alternatively or in addition to, brazing may be used to connect the wires to the insulation element. Both metallization and brazing, however, can lead to leaks over time.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1A:
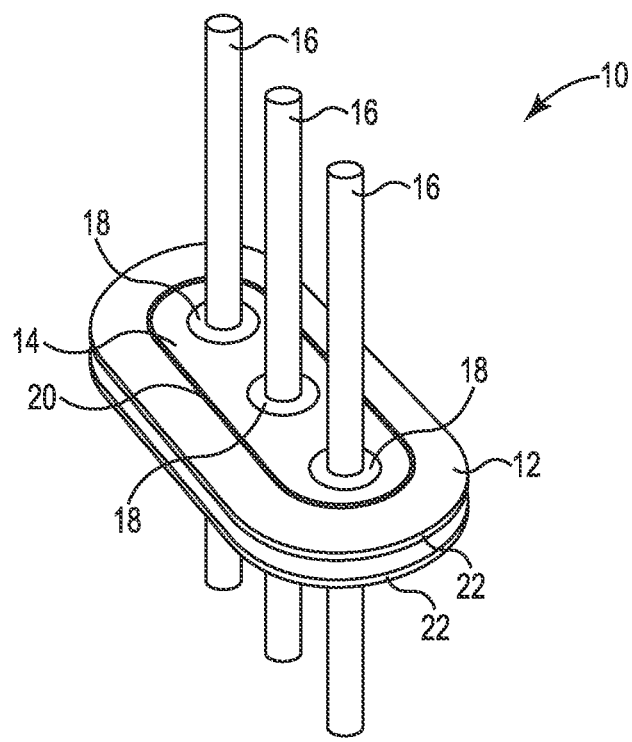
FIGS. 1A and 1B illustrate a feedthrough device in accordance with the prior art.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In accordance with one embodiment, a method of coupling an insulator to a surrounding ferrule in an implantable medical device is provided. An insulator is provided having a plurality of conducting elements extending therethrough. The insulator is placed with conducting elements within a ferrule having a frame-like shape surrounding the insulator along an interface. The insulator is heated with a first laser until raising the temperature of insulator to a first temperature level. The ferrule is welded to the insulator along the interface with a second laser once the insulator has reached the first temperature.

Normally, the energy level required to weld the ferrule to the insulator along the interface is so fast and locally restricted that the ceramic of the insulator would normally crack. Because the first laser first gradually raises the temperature of the ceramic insulator before the weld, however, the thermal shock of the welding is minimized.

In one embodiment, the temperature of the insulator is maintained with the first laser while the second laser welds the insulator to the ferrule. This can continue to maintain the reduction in thermal shock during welding to further minimize any cracking. In one embodiment, the first laser is controlled to scan the entire surface of the insulator.

In one embodiment, the conducting elements are provided in the insulator such that they do not extend past a surface of the insulator. As such, the first laser is able to scan the entire surface of the insulator without interference from the conducting elements.

In one embodiment, the insulator is provided free of braze such that the first laser is able to scan the entire surface of the insulator without melting any braze. As such, the hermeticity of feedthrough is not compromised by melting of braze.

In one embodiment, the first laser is a $CO_2$ laser configured to scan the insulator and bring its temperature up into the range of 1,300 to 1,600 degrees centigrade. In one embodiment, the first laser is controlled to ramp the temperature of the insulator from room temperature to between 1,300 and 1,600 degrees Centigrade at a rate of 100-150 degrees Centigrade per second. In one embodiment, the first laser is controlled to ramp down the temperature of the insulator at a rate of 100-150 degrees Centigrade per second until the temperature reaches 300 degrees Centigrade. Controlling the temperature in these ways can help prevent cracking the insulator material.

In one embodiment, the ferrule is provided with an inner edge that is tapered, wherein the insulator has an outer edge that is also tapered to match the inner edge of the ferule, which can provide advantages in holding the ferrule relative to the insulator during welding.

In one embodiment, a feedthrough for a medical implantable device includes a ferrule comprising a metal that is configured to be welded to a case of the implantable device. An insulator is substantially surrounded by the ferrule and shares an interface therewith. The insulator comprises a glass or ceramic material. Conductive elements are formed through the insulator providing an electrically conductive path through the insulator. There is no braze or solder at the interface between the ferrule and the insulator and there is no braze or solder adjacent the conductive elements. With no braze or solder at the interfaces, there is reduced risk of leak and the hermiticity of the feedthrough is preserved.

In one embodiment, the ferrule comprises one of a group comprising niobium, titanium, titanium alloy, molybdenum, cobalt, zirconium, chromium and platinum, the insulator comprises aluminum oxide and the conductive elements comprise a cermet. These materials allow the avoidance of any brazing to secure hermetic seals in the feedthrough.

In one embodiment, the ferrule is configured with an inner edge that is tapered and the insulator is configured with an outer edge that is tapered to match the inner edge of the ferule. In one embodiment, the taper of the respective edges of the ferrule and the insulator are tapered at an angle of 5 to 15 degrees relative to a line running perpendicular to a top surface of the feedthrough. The taper angle of the edges of the insulator and the ferrule at the interface allows the insulator to seat easily in the ferrule before the two are welded together along the interface. The taper angle of the outer edges of the insulator against the corresponding inner edges of the ferrule prevents relative movement of the ferrule and the insulator during assembly and welding.

In one embodiment, the distance between the ferrule and the insulator along the interface is no larger than 25 microns. Keeping the gap at the interface less than 25 microns minimized cracking of the insulator during welding.

In one embodiment, a method of welding an insulator in an implantable medical device in provided. An insulator is provided having a plurality of conducting elements extending therethrough. The insulator with conducting elements is placed within a metallic case surrounding the insulator at an interface. The insulator is heated with a first laser until raising the temperature of insulator to a first temperature level. The case is welded to the insulator with a second laser once the insulator has reached the first temperature.

Figure 1B:
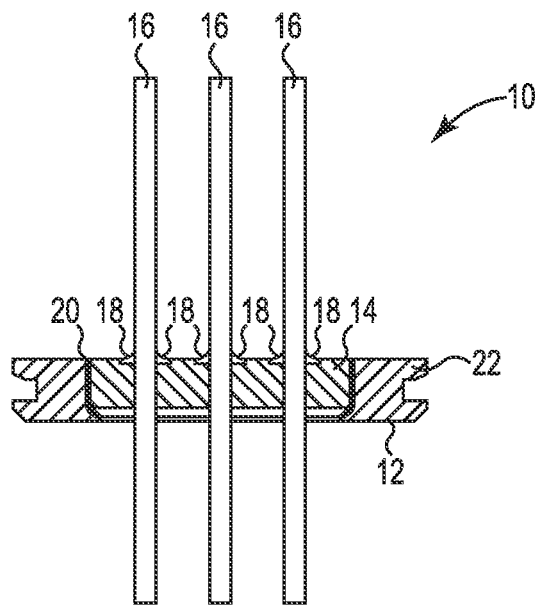

FIGS. 1A and 1B illustrate respective perspective and sectional views of feedthrough device 10, such as for an implantable medical device, in accordance with the prior art. Feedthrough device 10 includes ferrule 12, insulator 14 and feedthrough pins 16. Ferrule 12 is a frame-like structure with an internal opening into which insulator 14 is formed and through which feedthrough pins 16 extend. Insulator 14 facilitates feedthrough pins 16 extending through the frame-like structure of ferrule 12 in a non-conductive manner.

Ferrule 12 is configured to fit into an opening of a case for an implantable medical device and such that it can be tightly secured thereto in order to ensure a hermetic seal with respect to an internal space of the medical device. Feedthrough pins 16 extend from within the internal space of the case of the medical device to outside the device, thereby providing electrical connection from the inside to the outside, while maintaining a hermetic seal. Flanges 22 can be provided on ferrule 12 to further aid in securing feedthrough device 10 to the opening of the case of the implantable medical device and ensuring its hermetic seal.

Typically, insulator 14 is a ceramic or glass material, while ferrule 12 is metallic. Ferrule 12 is metallic so that it can be readily welded to a metallic case of the implantable medical device. In order for the ceramic material of insulator 14 to be coupled to the metallic material of ferrule 12, insulator 14 is typically "metalized" with metalized coating 20. Alternatively, a metallic braze is used to secure ceramic material of insulator 14 to the metallic material of ferrule 12. Similarly, braze 18 is used to couple the ceramic material of insulator 14 to feedthrough pins 16, which are metallic conductors.

Use of braze 18 to secure insulator 14 to feedthrough pins 16 and to secure insulator 14 to ferrule 12, and/or the need for metalized coating 20 to secure insulator 14 to ferrule 12 creates extra processing steps and adds to the complication and expense of manufacturing feedthrough device 10. Such braze 18 and metallization 20 can also lead to leaks and failure of a hermitic seal for feedthrough device 10.

Figure 2:
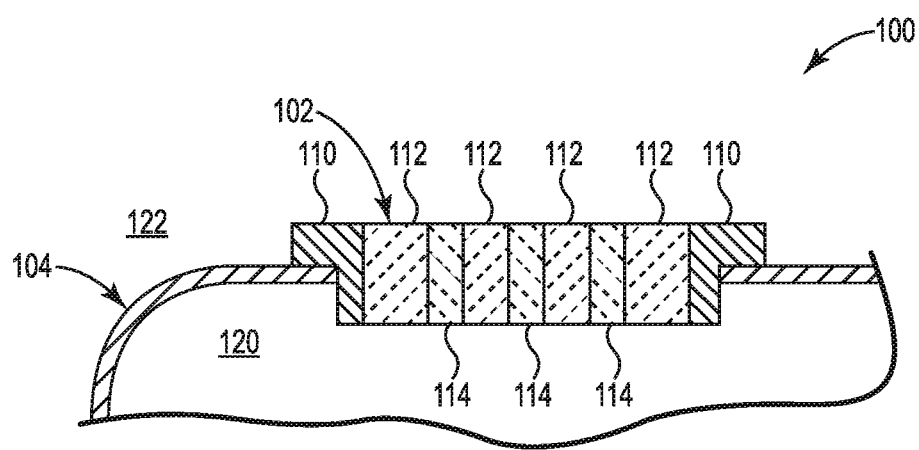
FIG. 2 illustrates a cross-sectional view of a feedthrough assembly in an implantable medical device in accordance with one embodiment.

FIG. 2 illustrates implantable medical device 100 in accordance with one embodiment. Implantable medical device 100 includes feedthrough assembly 102 and case 104. Feedthrough assembly 102 includes ferrule 110, insulator 112 and conducting elements 114. In one embodiment, ferrule 110 is a frame-like structure into which insulator 112 and conducting elements 114 are formed. In one embodiment, feedthrough assembly 102 is welded to case 104 such that an interior 120 of case 104 is hermetically sealed relative to its exterior 122.

In the exemplary embodiment according to FIG. 1, ferrule 110 is configured to be essentially frame-shaped and secured to case 104 thereby defining an internal space 120 and an external space 122. Ferrule 110 can be of a variety of shapes, for example, it can be a disc-shaped, round, an oval or a polygonal, in one embodiment a rectangular or square, cross-section in a sectional plane perpendicular to the drawing plane in FIG. 1. However, other cross-sections are also feasible as a general rule. The disc of ferrule 110 can be arranged, fully in the external space 122, in the internal space 120, or straddling the two as illustrated in FIG. 1.

In one embodiment, ferrule 110 of feedthrough assembly 102 is a metallic material, as is case 104, such that feedthrough assembly 102 is readily weldable to case 104. In one embodiment, conducting elements 114 are of an electrically conductive material such that they provide a conductive path from internal space 120 to external space 122 of case 104. Insulator 112 is of a non-electrically conductive material such that there is no conductive connection between ferrule 110 and conducting elements 114. All of the interfaces between insulator 112 and conducting elements 114 and between insulator 112 and ferrule must be sealed in such a way that a hermetic seal is maintained between internal space 120 and external space 122 of case 104. In one embodiment, all of these interfaces are so sealed without the use of braze or solder, as will be more fully explained below.

Figure 3A:
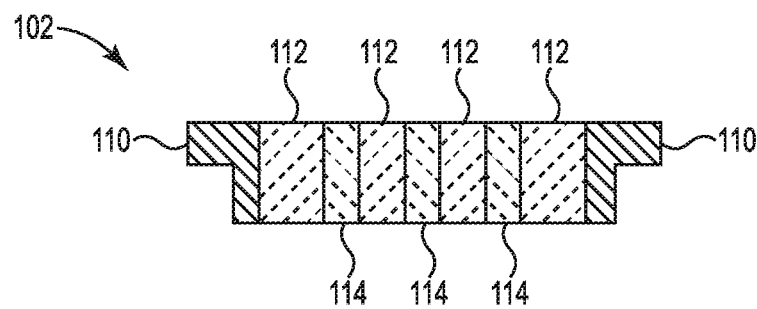
FIGS. 3A and 3B respectively illustrate cross-sectional and plan views of a feedthrough assembly in accordance with one embodiment.
Figure 3B:
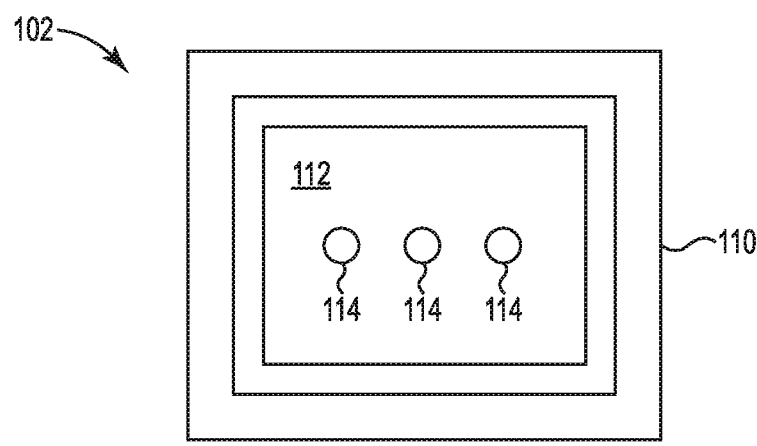

FIG. 3A illustrate a cross sectional view of feedthrough assembly 102 in accordance with one embodiment. FIG. 3B illustrates feedthrough assembly 102 viewed from a "lower" side relative to how it is depicted in FIG. 3A. In one embodiment, feedthrough assembly 102 is assembled by forming insulator 112 and conducting elements 114 in a first process. In one embodiment, insulator 112 is a ceramic material, such as aluminum oxide ($Al_2O_3$), and conducting elements 114 are a cermet material.

In the context of one embodiment, the terms, "cermet" or "cermet-containing," shall refer to all composite materials made of ceramic materials in a metallic matrix (binding agent). These are characterized by their particularly high hardness and wear resistance. The "cermets" and/or "cermet-containing" substances are cutting materials that are related to hard metals, but contain no tungsten carbide hard metal and are produced by powder metallurgical means. A sintering process for cermets and/or the cermet-containing elements proceeds just like with homogeneous powders with the exception that the metal is compacted more strongly at the same pressuring force as compared to the ceramic material. The cermet-containing bearing element has a higher thermal shock and oxidation resistance than sintered hard metals. In most cases, the ceramic components of the cermet are aluminum oxide ($Al_2O_3$) and zirconium dioxide ($ZrO_2$), whereas niobium, molybdenum, titanium, cobalt, zirconium, chromium and platinum are conceivable as metallic components.

The ceramic of insulator 112 can be, for example, a multi-layer ceramic sheet into which a plurality of vias is introduced. The cermet of conducting elements 114 is then introduced into the vias. In one embodiment, both materials are introduced in a green state, and as such, the combination is fired together. Accordingly, the joining of the insulator 112 and conducting elements 114 forms a hermetic seal therebetween without the use of braze or solder.

In accordance with one embodiment, insulator 112 is secured to ferrule 110 to form a hermetic seal therebetween, also without the use of braze of solder. In order to secure insulator 112 to ferrule 110, they are laser welded together. In one embodiment, a two-part laser welding process is used. In one embodiment, a first laser is scanned across insulator 112 in order to heat up the ceramic. Once an appropriate level of heat is reached, a second laser is used to perform a weld to join the insulator 112 to ferrule 110. In one embodiment, a first laser is used to scan both insulator 112 and ferrule 110 both before and after welding with a second laser.

Figure 4:
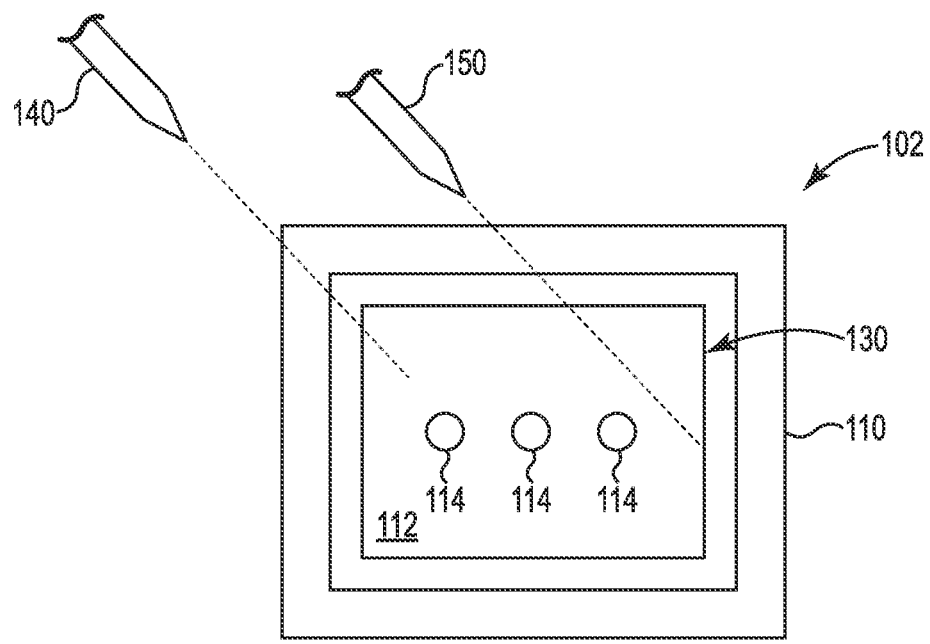
FIG. 4 illustrates a feedthrough assembly and method of forming in accordance with one embodiment.

FIG. 4 illustrates feedthrough assembly 102 in accordance with one embodiment. In one embodiment, ferrule 110 is joined to insulator 112 along interface 130 using a laser weld. In order to prepare interface 130 for a laser weld, a first laser 140 scans insulator 112 in order to raise the temperature of insulator 112. In one embodiment, first laser 140 is a $CO_2$ laser that is configured to scan over the ceramic material of insulator 112 in order to raise the temperature of the ceramic. In one embodiment, first laser 140 scans over insulator 112 to bring its temperature up into the range of 1,300 to 1,600 degrees centigrade.

Once this temperature range is achieved, a second laser 150 is used to weld along interface 130 between ferrule 110 and insulator 112. In one embodiment, second laser 150 is a YAG or fiber laser, which welds ferrule 110 to insulator 112 while first laser 140 maintains the temperature of insulator 112. Because second laser 150 produces a fast and locally restricted energy along interface 130, it would normally crack a material like ceramic of insulator 112. Accordingly, using first laser 140 to first raise the temperature of the ceramic of insulator 112 before application of the localized energy of second laser 150 minimizes the thermal shock of the welding by second laser 150.

In one embodiment, ferrule 110 is a material that is selected to have a coefficient of thermal expansion that is similar to that of the material of insulator 112. In one embodiment, insulator 112 is aluminum oxide ($Al_2O_3$) and ferrule 110 is niobium. Because aluminum oxide ($Al_2O_3$) has a coefficient of thermal expansion of $8.5 \times 10^{-6}$/C and niobium has a coefficient of thermal expansion of $8.7 \times 10^{-6}$/C, both materials will shrink a very similar amount after the heat of first and second lasers 140 and 150 is removed, such that there will be very little stress or cracking at the weld along interface 130. As such, the hermitic seal that is established by welding ferrule 110 to case 104 will not leak.

In one embodiment, a material selected for insulator 112 will have a coefficient of thermal expansion (CTE) that is within 25 percent of the CTE of the material selected for ferrule 110. In one embodiment, the CTE of the materials are kept similar, or within 25 percent of each other, such that the helium leak rate for implantable medical device 100, once feedthrough assembly 102 is secured to case 104, is less than 3.0E-09 Atm cc/sec.

In other embodiments, other metals with similar coefficients of thermal expansion can be used for ferrule 110 in conjunction with an aluminum oxide (Al2O3) insulator 112. For example, zirconium ($ZrO_2$) having a CTE of $8.6 \times 10^{-6}$/C, titanium (grade 2) having a CTE of $10.1 \times 10^{-6}$/C, and titanium-45 niobium (grade 36) having a CTE of $10.6 \times 10^{-6}$/C may also be used in some embodiments.

In one embodiment, first laser 140 is controlled to focus its energy on insulator 112 and also onto ferrule 110. Heating both the ceramic of insulator 112 and the metal of ferrule 110 before the weld can improve the quality of the weld. In one embodiment, it is also important that first laser 140 continues to maintain the heated temperature of insulator 112 while second laser 150 performs the weld at interface 130.

In one embodiment, ferrule 110 is particularly configured for heating with first laser 140 before welding with second laser 150. As illustrated in FIGS. 1A and 1B, a feedthrough device 10 having feedthrough pins 16 extending through insulator 14 will is not readily heated by a laser. Because feedthrough pins 16 extend well beyond the surface of insulator 14, they will tend to interfere with a laser that needs to scan the entire surface of the insulator in order to heat it up sufficiently before welding with another laser.

In addition, feedthrough device 10 also requires braze 18 to seal feedthrough pins 16 relative to insulator 14. As such, even if a laser were able to somehow navigate around feedthrough pins 16 to scan the entire surface of insulator 14, braze 18 would likely re-flow from the heat caused by the laser. Typically, braze 18 is a metal such as gold, and its melting point is below the temperature to which first laser 140 will heat the insulator and adjacent material, such as braze 18. This would very likely compromise the seal between feedthrough pins 16 and insulator 14 and potentially cause leaking.

As previously indicated, feedthrough assembly 102 in accordance with one embodiment includes conducting elements 114 that are introduced into vias within insulator 112. In some embodiments, conducting elements 114 may be configured to extend beyond the top and bottom surfaces of insulator 112, and in other embodiments, conducting elements can be configured to be flush with one or both surfaces. As illustrated in FIG. 3A, for example, conducting elements 114 are configured to be flush or aligned with both top and bottom surfaces of insulator 112. In this configuration, first laser 140 is able to readily scan the entire surface of insulator 112 without inference from anything projecting from the surface. Furthermore, because conducting elements 114 and insulator 112 are sealed with a co-sintering process such that no braze is used, scanning first laser 140 over the surface of insulator 112 will not cause problems in reflowing braze.

In one embodiment, the distance between ferrule 110 and insulator 112 along interface 130 is controlled such that the structures are snugly fitted before being welded by second laser 150. If a significant gap exists between ferrule 110 and insulator 112, some cracking can occur during the welding process. In one embodiment, the distance between ferrule 110 and insulator 112 at any location along interface 130 is no larger than 25 microns. As such, when the two materials are welded, cracking of insulator 112 is minimized.

Figure 5:
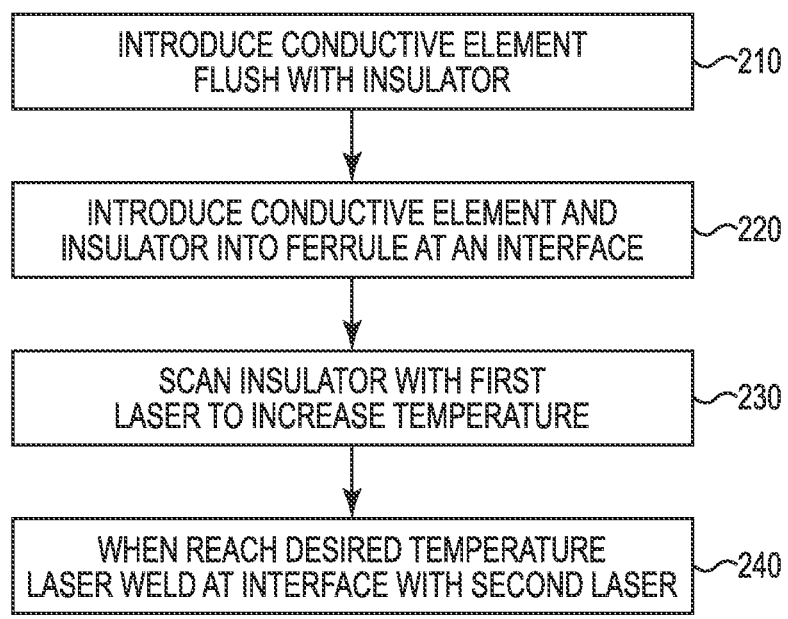
FIG. 5 illustrates a flow diagram of a method of forming a feedthrough assembly in accordance with one embodiment.

FIG. 5 is a flow diagram illustrating a process 200 of making a feedthrough assembly in accordance with one embodiment. In a first step 210, conductive elements are introduced into an insulator. In one embodiment, the conductive elements are either formed to be flush with the surfaces of the insulator or are milled or ground to be flush. At step 220, the conductive elements and insulator are placed in a frame-like ferrule. The insulator and ferrule are immediately adjacent each other forming an interface.

At step 230, a first laser is scanned over the entire surface of the insulator in order to bring up the temperature of the insulator. In one embodiment, the insulator is heated from room temperature to between 1,300 and 1,600 degrees Centigrade. In one embodiment, the first laser is controlled to ramp the temperature from room temperature to between 1,300 and 1,600 degrees Centigrade at a rate of 100-150 degrees Centigrade per second. In one embodiment, heating at this rate will not cause the insulator material to fracture or crack. In one embodiment, while the first laser is directed to scan the entire surface of the insulator, and in one embodiment is directed so as to additionally scan the ferrule that surrounds the insulator.

At step 240, a second laser is used to weld the ferrule to the insulator along the interface therebetween. In one embodiment, the first laser continues to scan the insulator, while the second laser welds the ferrule to the insulator, in order to maintain the temperature on the insulator. In one embodiment, the first laser continues to maintain the temperature of the insulator between 1,300 and 1,600 degrees Centigrade while the second laser welds the ferrule to the insulator. In one embodiment, once the entire interface is welded, the first laser is controlled to allow the temperature to ramp down at a controlled rate. In one embodiment, the first laser is controlled to ramp down the temperature at a rate of 100-150 degrees Centigrade per second until the temperature reaches 300 degrees Centigrade. Then, the first laser can be turned off or can be controlled to continue ramping down until the temperature reaches room temperature.

Figure 6:
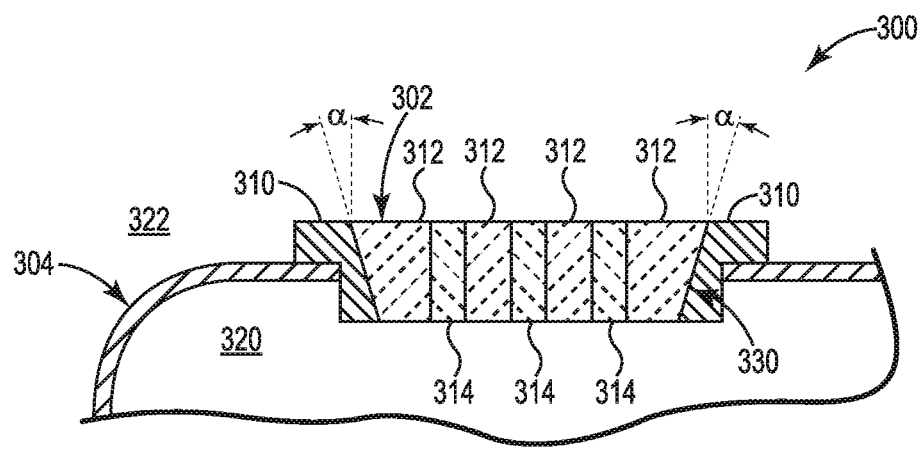
FIG. 6 illustrates a cross-sectional view of a feedthrough assembly in an implantable medical device in accordance with one embodiment.

FIG. 6 illustrates implantable medical device 300 in accordance with one embodiment. Implantable medical device 300 includes feedthrough assembly 302 and case 304. Feedthrough assembly 302 includes ferrule 310, insulator 312 and conducting elements 314. In one embodiment, ferrule 310 is a frame-like structure into which insulator 312 and conducting elements 314 are formed. In one embodiment, feedthrough assembly 302 is welded to case 304 such that an interior 320 of case 304 is hermetically sealed relative to its exterior 322.

In one embodiment, ferrule 310 has an inner edge that is tapered and insulator 312 has an outer edge that is also tapered to match the inner edge of ferule 310 at interface 330. In one embodiment, the edges at interface 330 are tapered at a taper angle α relative to a line running perpendicular to the top surface of feedthrough assembly 302. In one embodiment, taper angle α is between 5 and 15 degrees. In one embodiment, the taper angle α of the edges of insulator 312 and ferrule 310 at interface 330 allows insulator 312 to seat easily in ferrule 310 before the two are welded together along interface 330. The taper angle α of the outer edges of insulator 312 against the corresponding inner edges of ferrule 310 prevents relative movement of ferrule 310 and insulator 312 during assembly and welding.

In one embodiment, once insulator 312 is seated against ferrule 310, insulator 312 is heated with a first laser as described above with prior embodiments. After a temperature range is reached, a second laser is directed at the interface 330 between ferrule 310 and insulator 312 such that ferrule 310 is welded to insulator 312, similar to that described above with respect to feedthrough assembly 102.

Figure 7:
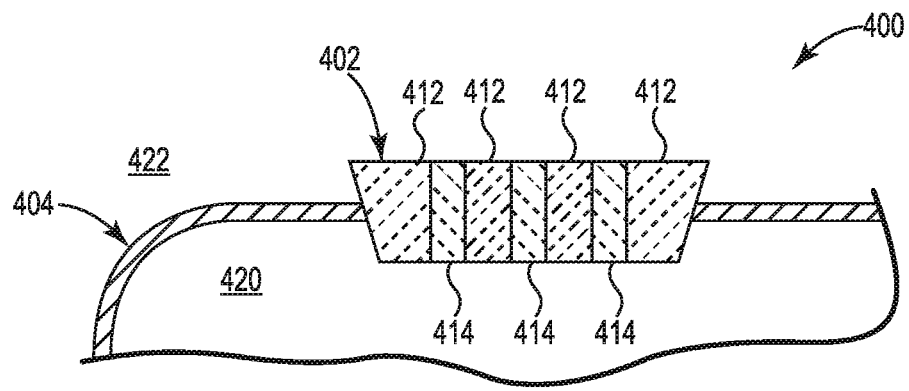
FIG. 7 illustrates a cross-sectional view of a feedthrough assembly in an implantable medical device in accordance with one embodiment.

FIG. 7 illustrates implantable medical device 400 in accordance with one embodiment. Implantable medical device 400 includes feedthrough assembly 402 and case 404. Feedthrough assembly 402 includes insulator 412 and conducting elements 414. As is evident from a comparison of FIG. 7 to FIG. 6 or FIG. 2, feedthrough assembly 402 does not include a ferrule such that insulator 412 is welded directly to case 404 such that an interior 420 of case 404 is hermetically sealed relative to its exterior 422.

In one embodiment, feedthrough assembly 402 includes insulator 412 with an outer edge that is tapered and case 404 has an inner edge that is also tapered to match the outer edge of insulator 412. Once feedthrough assembly 402 is placed in an opening of case 404, insulator 412 is heating with a first laser as described above with prior embodiments. After a temperature range is reached, a second laser is directed at the interface between case 404 and insulator 412 such that case 404 is welded to feedthrough assembly 402. Since case 404 is typically metallic, such as consisting of titanium, the second laser welds the metallic case to the insulator 412 similarly to that described above for how the ferrule and insulator are welded together.

Attaching feedthrough assembly 402 directly to case 404 without the need of a ferrule simplifies the assembly process and steps, reduces parts and material, and reduces overall time and cost.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of coupling an insulator to a surrounding ferrule in an implantable medical device comprising:
    providing an electrical insulator having a plurality of conducting elements extending therethrough;
    placing the insulator with conducting elements within a ferrule having a shape surrounding the insulator along an interface;
    heating the insulator with energy from a first laser until raising the temperature of the insulator to a first temperature level; and
    welding the ferrule to the insulator along the interface with energy from a second laser once the insulator has reached the first temperature.

2. The method of claim 1 further comprising maintaining the insulator at the first temperature with energy from the first laser while energy from the second laser welds the insulator to the ferrule.

3. The method of claim 1, wherein energy from the first laser is controlled to scan the entire surface of the insulator.

4. The method of claim 1, wherein the conducting elements are provided in the insulator such that they do not extend past a surface of the insulator such that energy from the first laser is able to scan the entire surface of the insulator without interference from the conducting elements.

5. The method of claim 1, wherein insulator is provided free of braze such that energy from the first laser is able to scan the entire surface of the insulator without melting any braze.

6. The method of claim 1, wherein energy from the first laser is emitted from a $CO_2$ laser configured to scan the insulator and bring its temperature up into the range of 1,300 to 1,600 degrees centigrade.

7. The method of claim 1, wherein energy from the first laser is controlled to ramp the temperature of the insulator from room temperature to between 1,300 and 1,600 degrees Centigrade at a rate of 100-150 degrees Centigrade per second.

8. The method of claim 1, wherein energy from the first laser is controlled to ramp down the temperature of the insulator at a rate of 100-150 degrees Centigrade per second until the temperature reaches 300 degrees Centigrade.

9. The method of claim 1, wherein ferrule is provided with an inner edge that is tapered, wherein the insulator has an outer edge that is also tapered to match the inner edge of the ferule.

10. A method of welding an insulator in an implantable medical device comprising:

providing an electrical insulator having a plurality of conducting elements extending therethrough;

placing the insulator with conducting elements within a metallic case surrounding the insulator at an interface;

heating the insulator with energy from a first laser until raising the temperature of the insulator to a first temperature level; and welding the case to the insulator with energy from a second laser once the insulator has reached the first temperature.

11. The method of claim 10 further comprising maintaining the insulator at the first temperature with energy from the first laser while energy from the second laser welds the insulator to the case.

12. The method of claim 10 wherein energy from the first laser is controlled to scan the entire surface of the insulator.

13. The method of claim 10 wherein the conducting elements are provided in the insulator such that they do not extend past a surface of the insulator such that energy from the first laser is able to scan the entire surface of the insulator without interference from the conducting elements.

14. The method of claim 10 wherein insulator is provided free of braze such that energy from the first laser is able to scan the entire surface of the insulator without melting any braze.

* * * * *